US011850280B1

United States Patent
van Oosterwijk et al.

(10) Patent No.: US 11,850,280 B1
(45) Date of Patent: Dec. 26, 2023

(54) ORAL VACCINE FOR PESTE-DES-PETITS-RUMINANTS VIRUS

(71) Applicant: US BIOLOGIC, INC, Memphis, TN (US)

(72) Inventors: Jolieke Gerdy van Oosterwijk, Memphis, TN (US); Andrew Raymond Peters, Dumfries Galloway (GB); Douglas Steven Zatechka, Jr., Cordova, TN (US); Luciana Meirelles Richer, Memphis, TN (US); Christopher Anthony Przybyszewski, Southaven, MS (US)

(73) Assignee: US Biologic, Inc, Memphis, TN (US)

( * ) Notice: Subject to any disclaimer, the term of this patent is extended or adjusted under 35 U.S.C. 154(b) by 252 days.

(21) Appl. No.: 17/218,939

(22) Filed: Mar. 31, 2021

Related U.S. Application Data

(60) Provisional application No. 63/007,275, filed on Apr. 8, 2020.

(51) Int. Cl.
    *A61K 39/155*      (2006.01)
    *C12N 15/75*      (2006.01)
    *C12N 7/00*      (2006.01)
    *A61K 39/00*      (2006.01)

(52) U.S. Cl.
    CPC ............. *A61K 39/155* (2013.01); *C12N 7/00* (2013.01); *C12N 15/75* (2013.01); *A61K 2039/542* (2013.01); *A61K 2039/55594* (2013.01); *A61K 2039/6087* (2013.01); *C12N 2760/18434* (2013.01)

(58) Field of Classification Search
    None
    See application file for complete search history.

(56) References Cited

U.S. PATENT DOCUMENTS

| | | | |
|---|---|---|---|
| 6,432,411 | B1 | 8/2002 | Ivy et al. |
| 10,087,451 | B2 | 10/2018 | Bermudes |

OTHER PUBLICATIONS

Apsana et al., Small Ruminant Research, 2016, 144:75-82. (Year: 2016).*
Balamurugan et al., Adv. Anim. Vet. Sci., 2016, 4(6): 301-310. (Year: 2016).*
Hardy et al., Nature, 1981, 293: 481-483. (Year: 1981).*
Alsafly et al. "Contrast Radiographic, Ultrasonographic and Computed Tomographic Imaging Studies on the Abdominal Organs and Fatty Liver Infiltration of Zaraibi Goat", J. Med. Sci. 13(5):316-326, 2013.
Baron et al "Peste des Petits Ruminants virus", Adv Virus Res. 95:1-42, 2016.
Chen et al "Vaccination Strategies to Promote Mucosal Antibody Responses", Immunity. 33:479-491, 2010.
Choppin et al The role of viral glycoproteins in adsorption, penetration, and pathogenicity of viruses, Rev Infect Dis. 2:40-61, 1980.
Fujkuyama et al Novel Vaccine Development Strategies for Inducing Mucosal Immunity, Expert Rev Vaccines. 11 (3): 367-379, 2012.
Grote et al "JCat: a Novel Tool to Adapt Codon Usage of a Target Gene to its Potential Expression Host", Nucleic Acids Research. 33(2):W526-W531, 2005.
Herbert et al "Recombinant adenovirus expressing the haemagglutinin of peste des petits ruminants virus (PPRV) protects goats against challenge with pathogenic virus; a DIVA vaccine for PPR", Vet Res. 45:24, 2014.
Herrero et al "The roles of livestock in developing countries", Animal. 7 Suppl 1:3-18, 2013.
Mariner et al. "The opportunity to eradicate Peste des Petits Ruminants", J Immunol. 196:3499-3506, 2016.
Mazzitelli et al. "Production and Characterization of Alginate Microcapsules Produced by a Vibrational Encapsulation Device", J. Biomat. Appl. 23:123-145, 2008.
Morbidelli et al. "A quick and simple method for the determination of Ivermectin in dog plasma by LC/MS", MethodsX. 5:1503-1507, 2018.
Neutra et al. "Mucosal Vaccines: the Promise and the Challenge", Nature Rev. Immunol. 6: 148-158, 2006.
Ogra et al. "Vaccination Strategies for Mucosal Immune Responses", Clin. Microbiol. Rev. 14(2): 430-445, 2001.
Rojas et al. "Vaccination with recombinant Adenoviruses Expressing the Peste des Petits Ruminants Virus F or H Proteins Overcomes Viral Immunosuppression and Induces Protective Immunity against PPRV Challenge in Sheep", PLoS One. 9(7): e101226, 2014.
Schulte-Herbruggen et al. "Rural protein insufficiency in a wildlife-depleted West African farm-forest landscape", PLoS One. 13;12(12):e0188109, 2017.
Woodrow et al. "Mucosal Vaccine Design and Delivery", Annu. Rev. Biomed. Eng. 14: 17-46, 2012.

* cited by examiner

*Primary Examiner* — Nicole Kinsey White
(74) *Attorney, Agent, or Firm* — Veritay Group IP, PLLC; Susan B. Fentress

(57) ABSTRACT

The inventive subject matter includes a viral-vectored composition made of a bacterial expression vehicle expressing one or more recombinant viral protein antigens and its method of use. In particular, this invention relates to a vaccine for oral administration. Preferably, the bacterial expression vehicle is *Bacillus subtilis*.

5 Claims, 10 Drawing Sheets
Specification includes a Sequence Listing.

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
atgtctgctc aacgtgaacg ta                                              22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ttaaacaggg ttgcatgtaa cttc                                            24

<210> SEQ ID NO 3
<211> LENGTH: 1830
<212> TYPE: DNA
<213> ORGANISM: Artificial Sequence
<220> FEATURE:
<223> OTHER INFORMATION: insert

<400> SEQUENCE: 3
atgtctgctc aacgtgaacg tatcaacgct ttctacaaag ataaccttca taacaaaaca      60
catcgtgtta tccttgatcg tgaacgtctt acaatcgaac gtccttacat ccttcttggc     120
gttcttcttg ttatgttcct ttctcttatc ggccttcttg ctatcgctgg catccgtctt     180
catcgtgcta cagttggcac agctgaaatc caatctcgtc ttaacacaaa catcgaactt     240
acagaatcta tcgatcatca aacaaaagat gttcttacac ctcttttcaa aatcatcggc     300
gatgaagttg gcatccgtat ccctcaaaaa ttctctgatc ttgttaaatt catctctgat     360
aaaatcaaat tccttaaccc tgatcgtgaa tacgatttcc gtgatcttcg ttggtgcatg     420
aaccctcctg aacgtgttaa aatcaacttc gatcaattct gcgaatacaa agctgctgtt     480
aaatctgttg aacatatctt cgaatcttct cttaaccgtt ctgaacgtct tcgtcttctt     540
acacttggcc ctggcacagg ctgccttggc cgtacagtta cacgtgctca attctctgaa     600
cttacactta cacttatgga tcttgatctt gaaatgaaac ataacgtttc ttctgttttc     660
acagttgttg aagaaggcct tttcggccgt acatacacag tttggcgttc tgatacaggc     720
aaaccttcta catctcctgg catcggccat ttccttcgtg ttttcgaaat cggccttgtt     780
cgtgatcttg aacttggcgc tcctatcttc catatgacaa actaccttac agttaacatg     840
tctgatgatt accgttcttg ccttcttgct gttggcgaac ttaaacttac agctctttgc     900
acaccttctg aaacagttac actttctgaa tctggcgttc ctaaacgtga acctcttgtt     960
```

-continued

```
gttgttatcc ttaaccttgc tggccctaca cttggcggcg aactttactc tgttcttcct   1020
acaacagatc ctacagttga aaaactttac ctttcttctc atcgtggcat catcaaagat   1080
aacgaagcta actgggttgt tccttctaca gatgttcgtg atcttcaaaa caaaggcgaa   1140
tgccttgttg aagcttgcaa aacacgtcct ccttctttct gcaacggcac aggcatcggc   1200
ccttggtctg aaggccgtat ccctgcttac ggcgttatcc gtgtttctct tgatcttgct   1260
tctgatcctg gcgttgttat cacatctgtt ttcggccctc ttatccctca tctttctggc   1320
atggatcttt acaacaaccc tttctctcgt gctgcttggc ttgctgttcc tccttacgaa   1380
caatctttcc ttggcatgat caacacaatc ggcttccctg atcgtgctga agttatgcct   1440
catatcctta caacagaaat ccgtggccct cgtggccgtt gccatgttcc tatcgaactt   1500
tcttctcgta tcgatgatga tatcaaaatc ggctctaaca tggttgttct tcctacaaaa   1560
gatcttcgtt acatcacagc tacatacgat gtttctcgtt ctgaacatgc tatcgtttac   1620
tacatctacg atacaggccg ttcttcttct tacttctacc ctgttcgtct taacttccgt   1680
ggcaaccctc tttctcttcg tatcgaatgc ttcccttggt accataaagt ttggtgctac   1740
catgattgcc ttatctacaa cacaatcaca aacgaagaag ttcatacacg tggccttaca   1800
ggcatcgaag ttacatgcaa ccctgtttaa                                    1830
```

ORAL VACCINE FOR PESTE-DES-PETITS-RUMINANTS VIRUS

REFERENCE TO A SEQUENCE LISTING

Filed herewith electronically and specifically incorporated by reference in its entirety, the material in the ASCII text file identifying the name of the ASCII text file (30010.0011), the date of creation (Apr. 6, 2020) and the size of the ASCII text file in bytes (340 KB (348,160 bytes)).

BACKGROUND OF THE INVENTION

(1) Field of the Invention

The presently disclosed subject matter relates to a composition and method of using the composition for oral administration of a bioactive agent to an animal subject. More particularly, the presently disclosed subject matter relates to a composition made of a substrate and an effective amount of the at least one bioactive agent layered over the substrate and a method for eliciting a mucosal immunological response to the at least one bioactive agent. The presently disclosed subject matter further relates to a method of preparing the composition in formulation for stability to bypass the rumen of ruminant subjects.

(2) Description of the Related Art

Zoonotic diseases account for 75% of all emerging infectious diseases with an incidence of 2.5 billion people a year and an annual mortality of 2.7 million. In addition, infectious diseases in livestock can pose a serious economic threat to the livelihood supported by farm operations, and infectious diseases affect both large, concentrated feed operations and small share-holder-type operations. Considering the etiology of infectious disease, approximately 75% of viruses and 50% of bacteria that have been identified as causal agents of disease in humans are zoonotic. Moreover, for diseases afflicting livestock, viral infectious agents are more prevalent than bacterial-based pathogens, spreading at a rate of nearly 3:1 among herd animals. Current strategies to control zoonotic infectious disease include the deployment and application of pesticides to eliminate the vector from the enzootic cycle. However, the use of pesticides presents with toxic off-target effects upon the host subject and environment. The use of prophylactic and therapeutic antibiotics has inadvertently led to the evolution of antimicrobial-resistant strains of infectious agents being introduced and subsequently maintained in the zoonotic cycle. Further, while targeting susceptible disease reservoir hosts with prophylactic or therapeutic agent campaigns often employ parenteral administration, such administrative methods pose cost and logistics challenges where support for cold chain and stability measures are needed to accommodate unique geographical regions. The use of an oral delivery platform aimed at vaccinating animals against infectious diseases can effectively reduce disease spread and animal mortality.

While the use of bacterial expression systems remains the principal platform for recombinant protein antigen expression, molecular engineering of constructs to facilitate the expression of viral-based antigens is uniquely supported in the context of the vaccine oral delivery platform as an opportunity to address diseases of vial origin in a spectrum of animals. The oral delivery platform can be formulated for the enteric stability of immunogenic protein antigens in both multi- and monogastric animals in an effort to appropriately control viral infectious spread.

Adapting the oral delivery platform for multi-gastric animals (ruminants) considered the goat as the animal model, with the ultimate goal of developing an oral vaccine against the Peste-des-Petits-Ruminants virus (PPRV), the causative agent of Peste-des-Petits-Ruminants (PPR). PPR is a highly contagious disease in small ruminants and is endemic in Africa, Asia, and the Middle East with aggressive epidemics recently reported in Eastern Europe (Baron et al., *Adv Virus Res.* 2016; 95:1-42, 2016). PPRV is a member of the genus Morbilliviridae, presents with a range of clinical symptoms, and is a notifiable disease with required reporting to the World Organization for Animal Health (01E). An acute illness mortality rate of 50-80% and asymptomatic disease transmission entitles PPR as a threat to economic stability and food security with the greatest burden on households that depend on livestock for their daily protein consumption (Herrero et al, Animal. 7 Suppl 1:3-18, 2013, Schulte-Herbrüggen et al., "Rural protein insufficiency in a wildlife-depleted West African farm-forest landscape", *PLoS One.* 13; 12(12):e0188109, 2017). In response to this threat, the OIE initiated a worldwide eradication effort (Mariner et al., *J Immunol.* 196:3499-3506, 2016).

Current PPR vaccination is performed using live attenuated PPRV, leading to protective serum level antibodies for up to three years (Baron et al., *Adv Virus Res.* 2016; 95:1-42, 2016). The limitations of using live attenuated vaccines are: 1) the need for a cold chain biologistics infrastructure, 2) the need for skilled veterinarians for vaccine injection, and 3) a lack of differentiation between infected and vaccinated animals (DIVA), an essential measure to evaluate vaccine success in the field. To address limitations in support of DIVA, novel vaccines are under development that use recombinant viral vectors expressing the PPRV membrane glycoproteins, such as PPRV-F (fusion protein) or PPRV-H (hemagglutinin protein), each of which support the utility of serum antibodies specifically raised against the viral vector as a unique signature for DIVA (Chen and Cerutti, *Immunity.* 33:479, 2010; Fujkuyama, et al., *Expert Rev Vaccines.* 11:367, 2012; Herbert and Baron, *Vet Res.* 45:24, 2014, Rojas et al., *PLoS One.* 9(7): e101226, 2014.). The targeted PPRV membrane glycoproteins expressed in the viral vectors are essential for viral adsorption and induce both humoral and cell-mediated immune responses in the host (Choppin and Scheid, *Rev Infect Dis.;* 2:40-61, 1980), making them candidates for vaccine development.

Adapting the oral delivery platform for mono-gastric animals considered the mouse as the animal model, with an extension of the platform for application in domesticated animals and humans.

The oral platform further demonstrates here its utility as a system in which to conduct preliminary vaccine trial assessments of various antigens to evaluate initial seroresponse measures as indicators of essential immunogenicity proof-of-concept (POC) in animal subjects targeted as models for controlling disease burden. By definition, any molecular structure or substance recognized by the immune system as unique or non-native, are labelled as a potential threat to the stable homeostatic physiological processes of the organism and therefore are defined as antigens that elicit an immunological response. The platform supports the use of molecular fluorescent visualization markers to include green fluorescent protein (GFP) tags and active pharmaceutical ingredients (APIs) as antigenic indicators for measures of success for considering the platform in the context of unique animal subjects. Such POC studies can be employed to evaluate the platform in targeted animal models in advance of considering the platform for support of the subsequent complex molecular engineering of antigen expression systems required that can present efficacious vaccines against unique infectious agents.

SUMMARY OF THE INVENTION

This summary describes several embodiments of the presently disclosed subject matter, and, in many cases, lists variations and permutations of these embodiments. This summary is exemplary of the numerous and varied embodiments and therefore, mention of one or more representative features of a given embodiment is likewise exemplary. Such an embodiment can typically exist with or without the feature(s) mentioned and correspondingly, those features can be applied to other embodiments of the presently disclosed subject matter, whether listed in this summary or not. To avoid excessive repetition, this summary does not list or suggest all possible combinations of such features.

The inventive subject matter includes a viral-vectored composition made of a bacterial antigen expression vehicle expressing one or more recombinant viral protein antigens. In particular, this invention relates to a vaccine for oral administration. Preferably, the bacterial expression vehicle is Bacillus subtilis.

This vaccine is a viral-vectored composition made of a bacterial antigen expression vehicle expressing one or more recombinant viral protein antigens. Preferably, the vaccine expresses one or more recombinant viral protein antigens molecular engineered biosynthetically from Peste-des-Petits-Ruminants virus (PPRV). Additionally, another feature of the one or more recombinant viral protein antigens is that they are molecular engineered to express immunomodulating agents, such as viral hemagglutinin fusion protein constructs (PPRV-H), or to include molecular adjuvants such as lipopolysaccharide biosynthesized from E. coli.

Oral administration is achieved by the formulation of a vaccine coated solid support. The vaccine coated solid support is made by stabilizing the one or more recombinant viral protein antigens within a liquid carrier matrix and a cross-linking agent to facilitate encapsulation of the one or more recombinant viral protein antigens on the surface of said solid support. Preferably the solid support includes a ruminant undegradable protein (RUP).

Another aspect of the invention is a process for producing one or more recombinant viral protein antigens expressed in the context of a bacterial antigen expression vehicle. This process includes the steps of: producing said bacterial expression vehicle by culturing a competent bacterium transformed with a replicable plasmid DNA expression construct for the expression of the viral protein antigens within the context of the said competent bacterium and expressing the one or more recombinant viral protein antigens in the bacterial expression vehicle.

Another aspect of the invention is a method of vaccinating a subject This method includes the steps of orally administering to the subject an immunogenically effective amount of a viral-vectored composition. The viral-vectored composition is made of a bacterial antigen expression vehicle expressing one or more recombinant viral protein antigens, wherein the viral-vectored composition is coated on a solid support

BRIEF DESCRIPTION OF THE DRAWINGS

The patent or application file contains at least one drawing executed in color. Copies of this patent or patent application publication with color drawing(s) will be provided by the Office upon request and payment of the necessary fee FIG. 1 shows a vector with PPR virus Hemagglutinin Protein Bacillus gene construct (arrow, SEQ ID 3).

FIG. 2 shows protein folding optimization with a molecular adjuvant.

FIG. 3 is a gel showing restriction enzyme digestion and PCR amplification.

DETAILED DESCRIPTION OF THE INVENTION

Figure 4:
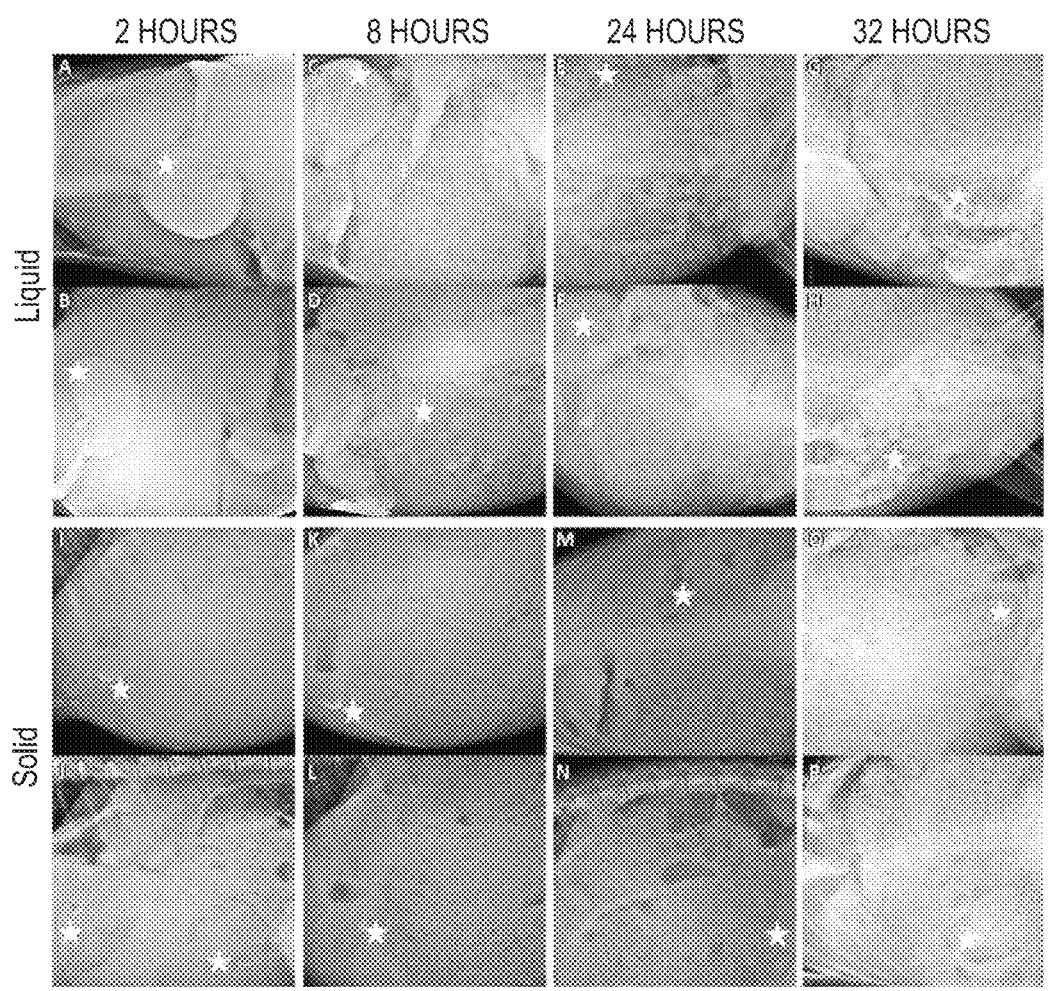
FIG. 4 shows intestinal tract with staining of the abomasum at two hours and manure staining in the small intestine starting at eight hours that intensified until 32 hours post administration.
Figure 5:
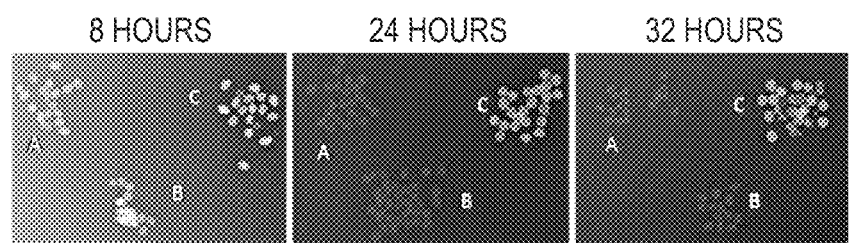
FIG. 5 shows image of barium in the goat manure.
Figure 6:
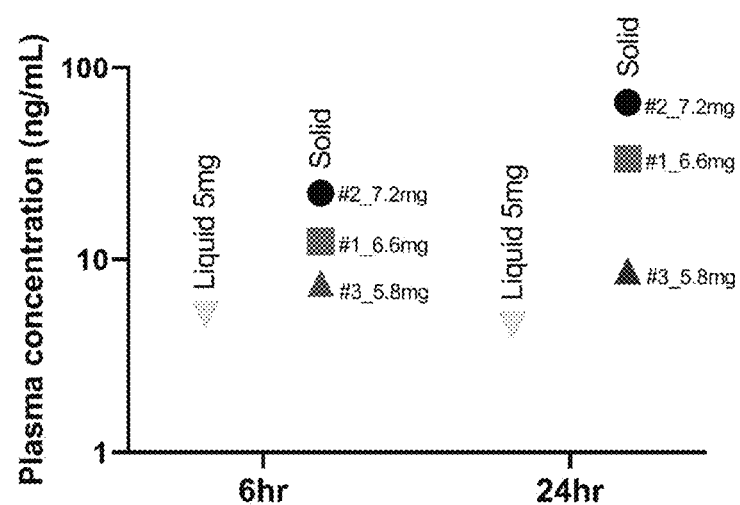
FIG. 6 shows plasma concentration versus time.

The details of one or more embodiments of the presently disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

While the terms used herein are believed to be well understood by one of ordinary skill in the art, definitions are set forth herein to facilitate explanation of the presently disclosed subject matter.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently disclosed subject matter relates to a composition and method of using the composition for oral delivery of a biologically active agent to a subject. More particularly, the presently disclosed subject matter relates to a composition made of a substrate and an effective amount of at least one biologically active agent stabilized by layered encapsulation over the substrate and a method of reducing infectious disease by administering the composition to a subject. The presently disclosed subject matter further relates to a method of preparing the composition.

In some embodiments of the presently disclosed subject matter, a composition is provided. The composition includes a substrate, an effective amount of an osmotically preconditioned at least one bioactive agent layered over the substrate, and a cross-linking agent. In some embodiments, the at least one bioactive agent is stabilized in a stabilizer under conditions facilitating anhydrobiosis.

The term "bioactive agent," "biologically active agent," "bioactive antigenic agent," "active pharmaceutical agent," refers to any substance that is of medical or veterinary therapeutic, prophylactic or diagnostic utility. In some embodiments, the bioactive agent includes a therapeutic agent. As used herein, a therapeutic agent refers to a bioactive agent that, when administered to a patient, will cure, or at least relieve to some extent, one or more symptoms of, a disease or disorder. In some embodiments, bioactive agent includes a prophylactic agent. As used herein, a prophylactic agent refers to a bioactive agent that, when administered to a patient either prevents the occurrence of a disease or disorder or, if administered subsequently to a therapeutic agent, prevents or retards the recurrence of the disease or disorder. In some embodiments, bioactive agent refers to a bacterial antigen expression vehicle for the expression of antigens that elicit an immune response, or proteins that can modulate the immune system, to enhance therapeutic potential. In some embodiments, the administration of the biologically active antigenic agent can elicit an immune response that is either prophylactic to prevent disease contraction and transmission, or therapeutic to resolve existing disease infection.

In some embodiments, the bioactive agent is a recombinant whole-cell bacteria molecular engineered to express one or more protein antigens. As used herein, the "recombinant whole-cell bacteria engineered to express one or more protein antigens" is a bacterial antigen expression vehicle for the expression of antigens. As used herein, "whole-cell bacteria" refers to bacterial cells, maintained under conditions that retain the bacterial cellular structural integrity, that is, whole-cell structural integrity and antigenicity, as a bioactive recombinant bacterial antigen expression vehicle that is an exogenous protein expression system for the stable presentation of antigen in certain embodiments. Conditions favorable for the structural integrity of the bioactive agent is defined as "stabilized." In certain embodiments, whole cells will be maintained as stable, not to be broken down into cellular fragments and/or other biological material and/or organelles. In maintaining the stabilized whole-cell structural architecture, some embodiments of vaccine preparation may encompass "active formulations," defined as live whole-cell bacterial units; other embodiments may encompass "inactive formulations," defined as killed whole-cell bacterial units termed bacterins. In some embodiments, stabilization refers to the process of bacterial sporulation. As defined and applied herein, sporulation refers to stability through metabolic inactivity.

In some embodiments, the whole-cell bacteria include, but is not limited to preparations of *B. subtilis*. As used herein, the bioactive agent, or biologically active agent, is a whole-cell bacterial antigen expression vehicle. As used herein cultures of *B. subtilis* are used as a collective homogeneous, clonally-expanded preparation of the bacterial antigen expression vehicle.

As used herein, bacterial antigen expression vehicles are considered biological vehicles, or biologics, wherein the composition is made of components of living biological organisms. The use of bacterial antigen expression vehicles as biologics that present with prophylactic and/or therapeutic intervention strategies in the control of disease has increased recently given the application of recombinant expression technologies. As a biologic, with added commensalism such as *Bacillus subtilis* have emerged in the biotechnology space as promising systems for recombinant protein expression technology given their GRAS (Generally Recognized As Safe) determination by the US Food and Drug Administration (FDA). However, *B. subtilis* strains are only now presenting with the expression systems supporting recombinant protein technologies. As such and given that *B. subtilis* is a commensal microorganism found in the GI tracts of both ruminants and humans, its utility as a bacterial antigen expression vehicle for orally delivered vaccine administration is shown in the presently disclosed subject matter.

In some embodiments, the bacterial antigen expression system bacteria are molecular engineered to express one or more antigens, which are expressed using a recombinant plasmid expression vector transformation event. As used herein, "molecular engineered" refers to the molecular biological technique of biosynthetic molecular cloning of genes identified for the expression of specific proteins of interest into the plasmid expression vector. As used herein, the plasmid expression vector is then used to transform a competent bacteria into the bacterial antigen expression system.

In some embodiments, the bacterial antigen expression system is vectored to express protein diagnostic tags. As used herein, such proteins are used in the processes of assaying and evaluating the functionality of the expression system in the context of a targeted administration subject. In some embodiments, the recombinant bacteria are engineered to express green fluorescent protein (referred to herein as GFP).

In some embodiments, the bacterial antigen expression system is a viral-vectored for the expression of biological antigens of viral origin. In some embodiments, a viral-vectored bacterial antigen expression system is engineered to provide a vaccine for oral vaccination. The term "viral-vectored bacterial antigen expression system" as used herein refers to the recombinant expression protein antigens derived from viral infectious agents of disease vectored in the context of the whole-cell bacterial antigen expression system for vaccination.

In some embodiments, the bacterial antigen expression system bacteria are molecular engineered to express one or more antigens from the Peste-des-Petits-Ruminants virus (referred to herein as PPRV), the causative agent of Peste-des-Petits-Ruminants (referred to herein as PPR).

In some embodiments, the recombinant viral protein antigens are molecular engineered to express immunomodulating agents. As used herein, immunomodulating agents refers to protein antigens that elicit a specific immunological response to the antigen in the form of serological antibody production. Examples of immunomodulating agents include, but are not limited to adjuvants. As used herein, an adjuvant is a substance that augments the immunological response to the vaccine antigen.

In some embodiments, the recombinant bacteria are lyophilized/freeze-dried. In some embodiments, the recombinant bacteria are air-dried as an anhydrobiotic preparation. In still other embodiments, the recombinant bacteria are rendered metabolically inactive via sporulation as an anhydrobiotic preparation. As used in the presently disclosed subject matter, the induction of anhydrobiosis is defined as a biologically stable state of desiccation, and as used herein is therefore a downstream bio-processing step introduced during production as a means to effectively dry the biologic product in a stable state to facilitate and accommodate the subsequent biologistics requirements.

Currently employed strategies for bulk anhydrobiotic processing include lyophilization (freeze-drying) of the biologic product resulting in a physical powder. However, the process of lyophilization can result in a significant loss of potency of whole-cell antigen expression vehicles for use as vaccines. Further, lyophilization is not easily scalable and can be costly for industrial application; as a powder, the resultant product must be further formulated for stability, application and administration as a vaccine.

Additional anhydrobiotic processing strategies have involved the use microencapsulation technologies for entrapping biologics in spheronized microbeads. Such technologies are employed in the processing of probiotic bacteria of the phylogenetic class Bacilli to include the lactic acid bacteria (LAB) and the *Bacillus* species for use in the probiotics industry. However, LAB are generally less efficient vehicles for recombinant protein expression, and thereby may not present as potent or efficacious vaccines. Further, the employment of downstream processing that results in the generation of microencapsulated biologics in the form of spherical microbeads, a product that presents as a course powder of beads the size of which may range from 100□m to several thousand □m, may not be of a size practical for targeted distribution as a reservoir targeted vaccine. Such beads are also of a composition of cellulose, specifically microcrystalline cellulose (MCC), a composition that may not be favorable for targeted (attractive) consumption as a bait by reservoir hosts.

Stability measures supporting oral administration of biologics employ the use of enteric protection for effective passage through the gut for specific release at targeted regions of the GI tract. The introduction of enteric stabilization methodologies has been utilized with success in the probiotics industry for administering efficacious doses of probiotic strains as part of a regimen for enhancing the gut microbiome and systemic health. Current strategies employ calcium-alginate encapsulation chemistries, wherein a given concentration of polymeric matrix made of the probiotic in composition with a solution of alginate are dripped via vibrational nozzle, or spray atomized, into a bath of a given concentration of a calcium salt facilitating a cross-linking (microencapsulation) of the polymeric matrix. The resultant microencapsulated probiotic product is retrieved from the calcium bath and subsequently lyophilized yielding the powdered final product for consumption. However, and as presented above, powdered formulations of biologics must be further downstream processed and formulated for application as vaccines. Powders will need to be applied with uniformity, for quality analysis and dosage standardization, as layers onto baiting substrate options. Such application may require added liquid carriers, drying measures, or physical applications to accommodate powders, all of which may be of detriment to the potency, and consequently, the efficacy of the bacterial antigen expression vehicle as a vaccine.

Vaccines must target the susceptible host of the disease or those hosts that are part of the enzootic disease cycle. Consequently, an oral administration material of a size and shape that promotes targeted consumption, targeted administration to the gut-associated lymphoid tissue, and at a scale that accommodates a mass distribution campaign, must be employed as an acceptable oral vaccine administration material for the host. This oral administration material, the substrate of which is summarized in the presently disclosed subject matter, is also a carrier for the administration of an orally delivered vaccine.

Inclusion of the bacterial antigen expression vehicle within the context of an oral administration substrate material requires a formulation that extends stability to the bacterial antigenic expression vehicle. The bacterial-expression vehicle may be sensitive to heat and pressure, which renders the biologic ineffective if formulated as an amalgam in composition and extruded with the substrate.

A composition and method is needed for the stable presentation of antigen, in the context of a whole-cell bacterial antigen expression vehicle, and administered in the context of a carrier substrate, as an orally administered vaccine for the control of infectious disease.

Specifically, a need exists where the passage and culture expansion of the bacterial antigen expression vehicle is reduced to practice for industrial application and scale in the absence of selectable antibiotic markers as a means to accommodate emerging new regulatory guidelines addressing anti-microbial resistance. In an increasing effort to control for the emergence of anti-microbial resistant bacterial strains, there is a continuously-improving sophistication surrounding the molecular biology techniques supporting biotechnology processes.

There is also a need for a unique downstream processing protocol that accommodates the unique biologic nature of the bacterial antigen expression vehicle as a means to osmotically precondition the vehicle for anhydrobiosis. As part of this preconditioning protocol, there is a need for establishing the composition and methods for the vehicle preconditioning process, to include the stability carrier matrix formulation and temperature parameters, and the subsequent application of the carrier matrix upon the carrier substrate.

Finally, as part of the process for stabilizing the bacterial antigen expression vehicle as a vaccine for oral administration, there exists a need for enteric stability for effective presentation of the vaccine antigen to specific regions of the gut of the targeted host.

In certain embodiments, the composition is a substrate and an effective amount of at least one bioactive antigenic agent coated or layered over the substrate. As used herein, the term "substrate" refers to a solid support composition, such as a carrier, onto which may be applied the stabilized vaccine composition.

In some embodiments, non-limiting examples of the bioactive antigenic vaccine agent include whole-cell bacteria as a biological vehicle of the antigenic agent. In some embodiments, the bioactive antigenic agent is osmotically pre-conditioned for anhydrobiosis and stabilization. As used herein, the term "osmotically preconditioned" refers to the use of specific solutes employed to physically stabilize and protect membranes and proteins in intact bacteria prior to drying to desiccation. Non-limiting osmotic preconditioners include plasticizing agents such as sugars, to include sucrose and/or trehalose, or hydroxyectoine. As used herein, the term "anhydrobiosis" refers to the physical state of biological tolerance to desiccation. Biological desiccation serves to maintain a biologically active composition, without water, thereby enhancing shelf life stability for extended vaccine potency.

In some embodiments, the bioactive antigenic agent is stabilized in a stabilizer. Stabilization refers to the means of promoting and maintaining the biological activity of the bioactive antigenic agent, wherein the whole-cell antigenic carrier is structurally maintained for effective presentation of antigen as an immunogen. Non-limiting stabilizers incorporate the use of hydrocolloids. As used herein, the term "hydrocolloid" will refer to any material of the colloid family of hydrophilic polymers dispersed in aqueous solution. Hydrocolloids present, in some embodiments, as small particles of about 1 to about 1000 nm in diameter, and serve to encapsulate and stabilize biological material. A hydrocolloid of the present disclosure may include, but is not limited to, agar, alginate, carrageenan, chitosan, gelatin, and/or gum.

Suitable hydrocolloids may include one or more natural and synthetic polymers, which form colloidal solutions in aqueous systems. Preferable hydrocolloids include polysaccharides, such as alginic acid, sodium alginate, and calcium alginate. Suitable hydrocolloids include polyvinyl pyrrolidones; starch; cellulose and cellulose derivatives, such as ethylcellulose, methyl cellulose, hydroxypropylmethyl cellulose (HPMC), hydroxypropyl cellulose (HPC), and carboxymethylcellulose (CMC); polyethylene glycol (PEG); or mixtures thereof.

As used herein, hydrocolloids are employed as liquid carriers for the at least one bioactive antigenic agent for feasible application as a liquid coating around the substrate. In some embodiments, the liquid carrier also serves to include application of visualization tracer formulations. As used herein, visualization tracer formulations include the divalent salts of barium, to include barium sulfate. As used herein, preparation of barium sulfate in the context of the liquid carrier stabilized by layered encapsulation over the substrate provide a means by which substrate administration formulation can be visualized via X-ray for gastro-intestinal (GI) dissolution. As used herein, GI dissolution further provides added assurance of the stabilization of the antigenic agent for presentation of the antigen payload to the gut-associate lymphoid tissues (GALT). In some embodiments, the liquid carrier also serves to include application of active pharmaceutical ingredients (APIs) as further measure of GALT dissolution and systemic metabolism of the liquid carrier stabilized by layered encapsulation over the substrate. As used herein, APIs can include, but are not limited to, the use of Ivermectin. As used herein, GALT-level dissolution of the API-liquid carrier stabilized by layered encapsulation can be measured via serological assay of Ivermectin by high-pressure liquid chromatography (HPLC).

In some embodiments, certain hydrocolloid polymers, such as sodium alginate, may be cross-linked in the presence of a calcium salt. Cross-linking in the presence of a divalent cation such as calcium refers to the capacity to structurally link the polymeric bonds of the hydrocolloid polymer, sodium alginate, to calcium to generate a polymer of calcium alginate cross-linked bonds; calcium ions replace the sodium ions in the alginate polymer yielding what is termed polymerization. Polymerization via cross-linking facilitates the stabilized encapsulation of the active vaccine agent as used in the presently disclosed subject matter.

In some embodiments, the cross-linking agent is a calcium salt. Examples of cross-linking agent include, but are not limited to, calcium lactate, calcium butyrate, calcium chloride, calcium sulfate, calcium carbonate, calcium acetate, or calcium ascorbate. As used in the presently disclosed subject matter, the cross-linking agent facilitates polymerization of the stabilizer.

As presented herein the composition of the presently disclosed subject, the composition relates to a composition made of a substrate and an effective amount of at least one biologically active antigenic agent stabilized by layered encapsulation over the substrate. As used herein, the term substrate relates to a substance of solid support, suitable for oral consumption, upon which or around which (as a shell or coating) may be applied the osmotically preconditioned stabilized at least one bioactive antigenic agent.

In some embodiments, the substrate has a mean diameter of from about 100 µm to about 5 cm. In some embodiments, the composition may be of a size of about no more than 10 cm to accommodate consumption by target animal species.

In some embodiments of the presently disclosed subject matter, examples of the substrate include, but is not limited to pellet, a chewable, a bead and a powder. In some embodiments, the substrate is a plant-based or earthen-based substance. In some embodiments, the earthen-based substance includes but is not limited to soil or water.

In some embodiments, the substrate further includes, but is not limited to, a plant and/or forage material to include grass, herbaceous legumes, tree legumes, silage, or crop residues to include grains such as corn or soybean stover, or other earthen-based substance, such as soil, compost, or addition directly to water. In certain embodiments, the substrate is edible, and appropriate to be fed to animals in a composition with a vaccine formulation. In some embodiments, the substrate may comprise a dried pellet or kibble, such as a particle generated by compressing original material, which may be broken up upon mastication into particulate material; and/or a chewable particle, soft and pliable in nature, such that it is not readily broken up or reduced to particulate matter upon mastication but may be readily dissolved; and/or a composition that may bypass the ruminant digestive processes such as a ruminant undegradable protein (RUP) substrate; micro-crystalline cellulose beads or other substrate for employment in the generation and application of vaccine in powdered formulation for administration via nasal inhalation, or to be administered directly to water as a hydrocolloidal suspension as an oral administration via drinking; a plant; a food-source, such as a food source that is available in the wild; and/or another earthen substance, soil or other onto which may be applied the active vaccine composition, which is then dried for stability, or water into which may be applied the active vaccine composition for consumption by drinking.

In some embodiments, the composition further includes a coating on the exterior surface of the composition. In some embodiments, the coating is an enteric coating. In some embodiments, the coating on the exterior surface of the substrate is sequentially applied in layers as a top-dressing and is an enteric coating once cross-linked.

In some embodiments, the substrate is in an amount of about 85% to about 99% w/w of the composition. In some embodiments, the stabilizer is in an amount of about 1% to about 15% w/w of the composition. In some embodiments, the effective amount of the bioactive agent is an immunogenically effective amount with the minimal immunizing dosage (MID) of about $5\times10^3$ CFU to about $5\times10^{11}$ CFU. In some embodiments, cross-linking agent is in an amount of about 0.5% to about 7.5% w/w of the composition. Further, in some embodiments, the coating is in an amount of about 1.5% to about 22.5% w/w of the composition.

Further, regardless of the particular mode and timing of administration used in accordance with the methods of the presently disclosed subject matter, the bacterium, including the bacterium-based compositions and antigenic agents described herein, are typically administered in an amount effective to achieve the desired response (i.e., protection against the antigenic agents). As such, the term "effective amount" is used herein to refer to an amount of the therapeutic composition sufficient to produce a measurable biological response (e.g., an immune response against PPR infection). In this regard, in some embodiments, the term "therapeutically effective" is used interchangeably herein with the phrase "immunogenically effective" to refer to an amount of whole-cell bacterial antigen expression vehicle expressing the at least one or more antigenic agent of the presently-disclosed subject matter sufficient to induce an effective immune response in a host against a virulent bacterium. Actual dosage levels of active ingredients in a therapeutic composition of the presently disclosed subject matter (e.g., the bacterium) can be varied so as to administer an amount of a composition that is effective to achieve the desired therapeutic response for a particular subject and/or application. Of course, the selected dosage level and amount of the bacterium and the other components of such a composition will depend upon a variety of factors including the activity of the bacterium, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art. As used herein, for example, in some embodiments, the therapeutic effective dose of the at least one antigenic agent is of a minimum immunizing dosage (MID) as measured in active antigen-expressing colony forming bacterial units (CFU) of about $5\times10^3$ to about $5\times10^{11}$ CFU.

In some embodiments of the presently disclosed subject matter, a composition for oral delivery of a bioactive agent is provided. The composition includes a substrate, an effective amount of at least one bioactive agent coated or layered on a substrate, and a cross-linking agent to facilitate the encapsulation of the antigenic in the stabilizer on the surface of the substrate. In some embodiments, the at least one bioactive agent is stabilized in a stabilizer selected from a group consisting of a hydrocolloid polymer further made of a plasticizing sugar to include sucrose. In some embodiments, the bioactive agent is an antigenic agent.

Still further, in some embodiments, a method of preparing a composition for oral delivery of a bioactive agent is provided. The method includes the steps of uniquely passaging and culturing the at least one antigenic agent; osmotically preconditioning the at least one antigenic agent; stabilizing at least one antigenic agent in a stabilizer; coating the stabilized at least one antigenic agent on to a substrate; applying a cross-linking agent; cross-linking to facilitate gelation or encapsulation of antigenic agent; and drying under forced air at an ambient temperature. In some embodiments, the temperature is in a range of between about −50° C. to about −80° C. In some embodiments, the temperature is in a range of between about 0.03 mBar to about 0.0005 mBar. In some embodiments, the temperature is in a range of between about 20° C. to about 35° C. In some embodiments, a fan drives the ambient temperatures. In some embodiments, the methods further include a step of coating with a confectionary glaze layer on the exterior surface for moisture barrier or flavored attractant. In some embodiments, the method further includes a step of coating with a shellac layer on the exterior surface for moisture barrier.

Current methods for generating calcium-alginate encapsulated biological materials require the generation of hydrogel or calcium-alginate beads. Bead-encapsulated biological materials are generated by the pressurized dispensing of sodium alginate into a volume of calcium salt, a process employing specific encapsulation equipment (an encapsulator) (Mazzitelli et al., *J. Biomat. Appl.* 23:123, 2008). Calcium-alginate beads generated by an encapsulator can be harvested and dried for downstream application. The bead format does not render itself beneficial or efficient for the uniform application onto defined substrates for targeted distribution and administration. Ibid.

Examples of encapsulation of antigens for oral administration include the following issued patents. For example, U.S. Pat. No. 5,352,448 describes the formulation and generation of hydrogels that can be loaded with antigen for oral administration as a hard, glassy bead. Additionally, U.S. Pat. No. 5,900,238 similarly describes the formulation and generation of antigen-encapsulated hydrogel microbeads for mucosal vaccination. Further examples include WIPO Pat. No. WO 2013/096883, which presents the methods for generating a spray-dried microencapsulated biological moieties and chemicals in polymers cross-linked by multivalent ions.

The presently disclosed subject matter provides a method of preparing a composition for oral delivery of a biologically active antigenic agent. The method includes, for example, the steps of: stabilizing by osmotic conditioning at least one antigenic agent, coating the at least one antigenic agent onto a substrate employing a sodium alginate suspension as a liquid carrier for layered application, cross-linking by a secondary layering of a calcium salt to facilitate layered gelation via calcium-alginate encapsulation of the bacterial antigen expression vehicle, and air drying under forced air ambient temperatures yielding a layered anhydrobiotic preparation of the biologically active antigenic agent. In some embodiments, the methods of the present disclosure include a step of coating the bacterial antigen expression vehicle and/or the substrate with a glaze layer on the exterior surface to provide a moisture barrier and/or flavored attractant. As such, employment of the more simplified sequential spray coating and layering application of the encapsulated biological materials provides an efficient and commercially viable method for the applying stabilized biologically active materials as layered coatings over a substrate. Encapsulated layering onto substrates provides a carrier method for targeted distribution of the biologically active agent.

In some embodiments, the presently disclosed subject matter relates to composition and methods for the stable expression of antigens for mucosal administration, more particularly, relates to oral administration to a subject such as a mammal to include a ruminant.

Further, in some embodiments, the methods of the present disclosure include a step of including in the coating a visualization tracer formulation within the context of the exterior surface of the bacterial antigen expression vehicle and/or of the substrate to provide a method for enterically visualizing the dissolution of the substrate administration formulation. As used herein, the composition of the presently-disclosed subject matter that includes the visualization tracer provides a composition and method for a marker vaccine to assess a differentiation of infected and vaccinated animals (DIVA). Response to infection elicits the processing and presentation of immunogenic antigens from the pathogens in the same process as the response elicited from the antigens derived from the vaccine. As used herein, the composition to include GFP will elicit an antigenic response unique from that which is elicited in response to both infected and vaccinated animals.

In some embodiments of the presently disclosed subject matter, the active vaccine agent is passaged in xxYT media (tryptone broth with yeast extract and sodium chloride, with xylose as selective agent at a concentration not to exceed 2%) at 30° C.±2° C. under constant agitation at 200 rpm until OD600 nm=2.5. As used in the presently disclosed subject matter, the biomass is washed free of culture fluids by suspension in phosphate-buffered saline (PBS; 0.8% Sodium Chloride, 0.02% Potassium Chloride, 0.144% Sodium Phosphate Dibasic, 0.024% Potassium Phosphate Monobasic).

In some embodiments of the presently disclosed subject matter, the active vaccine agent is osmotically preconditioned at for sporulation during 24 hours at 37° C., 200 rpm, in about 0.8% Nutrient Broth, 0.1% KCL, 0.1M each of $MgSo_4$ and $FeSO_4$, 1M $MnCl_2$, and 0.05M $CaCl_2$, dissolved in double distilled water, and purified using lysozyme. Pre-conditioned active agent is then mixed into a matrix of about 1.0% to about 2.5% sodium alginate in suspension with about 500 mM to about 625 mM sucrose, which is then applied onto the surface of the substrate by spray coating. A secondary layering of about 60 mM to about 500 mM concentration of a calcium salt is applied onto the surface of the substrate by spray coating. In some embodiments, the secondary layer is applied to the surface of the substrate about 1 second to about 60 seconds after application of the first layer. As used in the presently disclosed subject matter, the calcium salt is calcium lactate. In some embodiments, the calcium salt can be calcium butyrate, calcium chloride, calcium sulfate, calcium carbonate, calcium acetate, or calcium ascorbate.

The presently disclosed subject matter, in some embodiments, provides a method of controlling infectious diseases by vaccinating a subject at risk for being a carrier and/or symptomatic host thereof. The method includes orally administering to the subject a composition as disclosed herein. In some embodiments, the presently disclosed subject matter relates to a method of orally administered biological-based vaccines utilizing antigen-expression systems made of vectored bacteria that, upon consumption, elicit an immune response in targeted mammalian populations.

The present disclosure also relates to methods of stabilizing the active biological agent/component of a vaccine such that antigenic activity may be preserved and measured as a dosage; that the dosage maintains antigenicity for absorption by the immunologically-active GALT (gut-associated lymphoid tissue) or NALT (naso-pharyngeal-associated lymphoid tissue); and that the immunological response yields a reaction to the vaccine that is sustained, measurable, and prophylactic or therapeutic in the level of sero-responsiveness as assayed by antibody titers. Antibody titers are transmissible as prophylactically active compounds to neutralize targeted zoonotic incidence of infection.

Related to a method of use for the presently disclosed subject matter, animal mucosal surfaces present as principle entry sites for many infectious agents. Consequently, mucosal immunity offers an initial line of defense against infectious agents. The mucosal immune response interferes with the infectious process by hindering pathogen attachment to the mucosal epithelium, neutralizing viral and bacterial agents, and providing the means by which to remove pathogens through phagocytosis. The mucosal-associated immune system functions to prevent microbial penetration and infection through the internal regions of the animal. Because of the extensive immunological nature associated with the mucosal immune system, the region is also effectively targeted for vaccine administration to elicit prophylactic immunoresponsiveness against several pathogens (Chen and Cerutti, *Immunity.* 33:479, 2010; Fujkuyama et al., *Expert Rev Vaccines.* 11:367, 2012; Neutra and Kozlowski, *Nature Rev. Immunol.* 6:148, 2006; Ogra et al., *Clin. Microbiol. Rev.* 14:430, 2001; Woodrow et al., *Annu. Rev. Biomed. Eng.* 14:17, 2012).

The local immune response is most effectively induced in response to direct application of antigens to the mucosal surface. The site-specific presentation of antigens in native conformation, however, presents a challenge in terms of the available administrative vehicles that present as bacterial antigen expression vehicles and the toxicity associated with the antigens. Therefore, local immunity may be induced via the stimulation of the mucosa-associated lymphoid tissue (MALT), an integrated network of immunologically active mucosal tissue. Exposure by antigen at the mucosal surfaces of the gut or lung triggers the complex migration of lymphocytes to all mucosal regions where production of antigenic-responsive antibodies are produced. Antigenic exposure further induces a population of memory lymphocytes, which serve to generate antibodies in response to subsequent exposure by the same antigen. Hence, the MALT presents as a target for effective vaccination, by triggering the local immune response (Chen and Cerutti, Immunity. 33:479, 2010; Fujkuyama et al., *Expert Rev Vaccines*. 11:367, 2012; Neutra and Kozlowski, *Nature Rev. Immunol.* 6:148, 2006; Ogra et al., *Clin. Microbiol. Rev.* 14:430, 2001; Woodrow et al., *Annu. Rev. Biomed. Eng.* 14:17, 2012).

Of the immunologically active mucosal surfaces, the MALT of the gut-associated lymphoid tissues (GALT) in the intestines presents with the greatest accumulation of lymphoid tissue. GALT contains populations of functional T and B lymphocytes in conjunction with antigen-presenting accessory cells. Specifically, the B lymphocyte population of the GALT is a significant subset of cells committed to the generation of the immunoglobulin A (IgA) class of antibodies. As a neutralizing antibody, the localized availability of IgA of the GALT provides an effective means of preventing invading pathogens from attaching and penetrating the epithelial layer of the mucosal surfaces. This form of immunoresponsiveness differs from that of the systemic lymphoid tissues where the IgA antibody class is not effectively induced through the conventional intramuscular (IM) or subcutaneous (SubQ) methods of immunization administration (Chen and Cerutti, Immunity. 33:479, 2010; Fujkuyama et al., *Expert Rev Vaccines*. 11:367, 2012; Neutra and Kozlowski, *Nature Rev. Immunol.* 6:148, 2006; Ogra et al., *Clin. Microbiol. Rev.* 14:430, 2001; Woodrow et al., *Annu. Rev. Biomed. Eng.* 14:17, 2012).

An epithelial cell layer of the GALT separates the underlying lymphoid layer of the mucosa from the lumen of the gut. Interspersed within the epithelial layer are accessory cells with a committed function for antigen presentation. Such accessory cells actively sample luminal antigenic samples, internalizing the samples for processing and presentation to the adjacent lymphoid cells. Presentation and exposure of antigen to the GALT initiates the clonal expansion of antigen-specific B and T lymphocytes. The IgA-committed B lymphoblasts consequently migrate through the roesenteric lymph nodes, by means to trigger an enhanced specific immune response in all mucosal sites, including the intestinal tract, nasopharyngeal and respiratory tracts, lung, oral cavity, ocular regions, mammary gland, and genitourinary tract. Therefore, immuno-stimulation of the GALT through oral vaccination may consequently result in the prevention of infectious diseases at a variety of mucosal surfaces (Chen and Cerutti, Immunity. 33:479, 2010; Fujkuyama et al., *Expert Rev Vaccines*. 11:367, 2012; Neutra and Kozlowski, *Nature Rev. Immunol* 6:148, 2006; Ogra et al., *Clin. Microbiol. Rev.* 14:430, 2001; Woodrow et al., *Annu. Rev. Biomed. Eng.* 14:17, 2012).

In accordance with an embodiment of the present disclosure, animals are vaccinated via oral administration with hydrocolloid-stabilized/encapsulated whole-cell bacterial antigen expression vehicles coated onto edible delivery substrates.

Successful and efficacious orally administered vaccines require stability of the antigen as it passes through the digestive tract. As functional proteins dependent upon conformational structure, the configuration of antigens can be denatured under the digestive process of the gut. Enteric drug-delivery systems have been developed to protect the pharmaceutically active compounds for passage to the intestine. Moreover, hydrocolloids are useful for whole-cell encapsulation and/or for maintenance of cellular enzymatic reaction potential. In some embodiments of the present disclosure, hydrocolloids are, by virtue of their chemical and physical properties, employed as an enteric coating(s) for stabilizing the whole-cell antigen for effective presentation to the MALT. Hydrocolloids, such as alginates, offer a hydrophilic gel-network stabilization matrix that allow protection of encapsulated biologics for effective passage to targeted mucosal tissues, such as the GALT.

In some embodiments, the presently disclosed subject matter provides a method for effectively stimulating a mucosal immune response to presented antigen. Specifically, the present disclosure relates, in certain embodiments, to the use of hydrocolloid-stabilized bacterial antigen expression vehicle, such as whole-cell bacteria, as vaccines for the expression of antigens in native conformation. This presently disclosed subject matter further relates to methods of complexing the stabilized bacterial antigen expression vehicle in combination with compositions of substrates that facilitate delivery of the antigens to the mucosal-associated lymphoid tissues, via oral, and/or nasal administration.

Further provided, in some embodiments, is a method of controlling infectious diseases by vaccinating a subject in need thereof. The method includes orally administering to the subject a composition. The composition includes an effective amount of at least one bioactive agent layered over the substrate, wherein the at least one bioactive agent is stabilized in a stabilizer under conditions facilitating anhydrobiosis, and a cross-linking agent.

The presently disclosed subject matter, in some embodiments, provides a method of controlling infectious diseases by vaccinating a subject in need thereof. The method is adding a composition directly to a water supply in a suspension suitable for drinking. The composition includes an effective amount of at least one bioactive agent layered over the substrate, wherein the at least one bioactive agent is stabilized in a stabilizer under conditions facilitating anhydrobiosis, and a cross-linking agent.

In some embodiments, the presently disclosed subject matter provides an oral vaccine composition for reducing infectious disease, to include vector-borne and/or other zoonotic infectious diseases. As used herein, the term "zoonotic" or "zoonosis" refers to an infectious disease that may be transmitted between species. In some embodiments, infectious disease transmission may be facilitated by a disease-transmitting vector, to include, but is not limited to an insect (mosquito or other) and/or arthropod (tick or other). In some embodiments, zoonotic disease is vector-borne.

As used herein, "vectors" are living organisms that can transmit infectious diseases between humans or from animals to humans. Many of these vectors are bloodsucking insects, which ingest disease-producing microorganisms during a blood meal from an infected host (human or animal) and later inject it into a new host during their subsequent blood meal. "Vector-borne diseases" are illnesses caused by pathogens and parasites in animal and human populations. Vector-borne and other types of zoonotic infectious disease include, but are not limited to PPR, Bovine tuberculosis, Swine influenza virus, Dengue Fever, or Malaria.

In some embodiments of the presently disclosed subject matter, a method of controlling infectious disease by vaccinating a subject in need thereof is provided. The method is orally administering to the subject a composition made of a substrate and an effective amount of at least one active agent coated or layered over the substrate.

In some embodiments, the subject is a ruminant host of the zoonotic infectious disease cycle. In some embodiments, the subject is a susceptible host of the zoonotic infectious disease. In some embodiments, the subject is a xenodiagnostic carrier. Non-limiting examples of the subject include an arthropod, an insect, a mammal, a bird, a fish, and/or a domesticated or companion animal. In some embodiments, the mammal includes a feral animal including one or more of a mouse, a chipmunk, a squirrel, a shrew, a vole, a rat, a raccoon, an opossum, a skunk, a rabbit, and a deer. In some embodiments, the subject is a domesticated animal. In some embodiments, the domesticated animal is one or more non-limiting ruminant species to include members from cattle, sheep, a goat, and buffalo. In some embodiments, the domesticated animal is one or more non-limiting monogastric herbivore species to include members from horses, rabbits, gerbils and hamsters. In some embodiments, the domesticated animal is one or more non-limiting monogastric *omnivore* species to include members from humans, monkeys, rats, dogs, cats, and pigs. In some embodiments, the subject is a non-domesticated animal. In some embodiments, the non-domesticated animal is one or more non-limiting ruminant species to include members from deer, elk, moose. In some embodiments, the subject is a bird. In some embodiments, the subject is a fish.

As used herein, the term "reservoir host" refers to an organism harboring infectious disease microorganisms or pathogens, but presenting as asymptomatic. Specifically, as referred to herein, the reservoir host serves in the transmission cycle of zoonosis by harboring infectious agents that may be transmitted to other reservoir hosts, or subsequent susceptible hosts. In some embodiments, a reservoir host may transmit an amount of an infectious agent to, for example, a feeding vector, which may be transmitted to a subsequent reservoir host and/or subsequent susceptible host.

As used herein, the term "susceptible host" refers to an individual organism that is predisposed, vulnerable, and/or receptive to disease. Specifically, as referred to herein, the susceptible host is receptive to the disease transmitted by a disease-harboring vector carrier. Specifically, as referred to herein, the term "xenodiagnostic carrier" may be employed to describe a diagnostic method to document the presence of infectious disease-presenting microorganisms, or pathogens, by exposing potentially infectious tissue to a naïve vector, and then assaying the vector for the presence (ingested) of the same infectious agent(s).

The presently disclosed subject matter is further illustrated by the specific but non-limiting examples provided herein. Moreover, the following examples may include compilations of data that are representative of data gathered at various times during the course of development and experimentation related to the present disclosure.

Methods and results disclosed herein are provided to report an analysis of vaccine efficacy. An efficacious vaccine is defined as one that induces a sustained immune response based upon a designated administration protocol. Immunoresponsiveness is dependent upon the presentation of an antigen to the immune system. For the present disclosure, antigenic presentation considers the utility of a biological system, a maintained bacterial whole-cell bacterial antigen expression vehicle whereby said antigen is stably expressed on the cell surface for effective presentation to the immune system upon administration. Bacterial expression systems further present as natural adjuvants for use in the enhancement of the vaccine-induced immune response. The following testing measures are employed to assay for the effectiveness of the vaccine; the embodiment below encompasses the candidate vaccine for PPR. Testing involves assaying for bacterial strain identity and purity, plasmid sequence based upon restriction digestion and sequencing, and protein expression following the standard operating procedures for the sterility testing of modified live biological products in accord with 9 CFR 113.27(b). Vaccine efficacy validation and testing further follows that which is in accord with VSM 800.202

EXAMPLES

Examples specifically incorporate by reference Patent No. 10,653,630 "Composition and Method for Reducing Zoonotic Infectious Diseases" in its entirety.

Example 1—Vaccine Antigen Expression System

The following study relates to the methods for engineering the expression of viral-based antigens vectored in bacterial antigen expression vehicles as vaccines for oral administration.

For immunogenicity trials, *E. coli* and *B. subtilis* were used as bacterial antigen expression vehicles for antigen expression. For safety considerations, *E. coli* was inactivated prior to administration, and *B. subtilis* was engineered for recombinant protein expression without an antimicrobial resistance marker, and for deficiency of proliferation outside the laboratory. Goats were randomly assigned to treatment groups.

Figure 1:
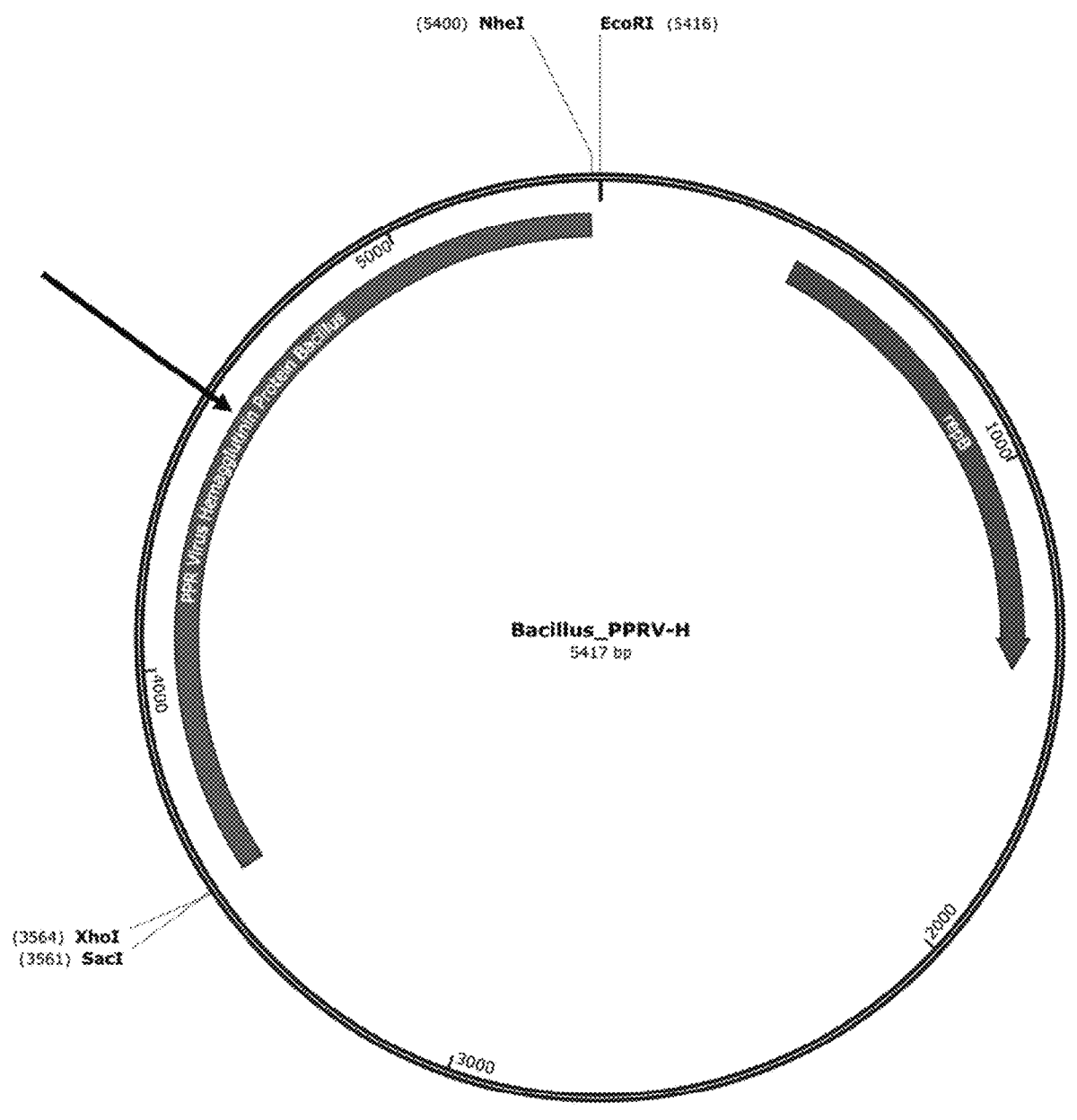

GFP and PPRV-H (small ruminant morbillivirus strain 75/1, hemagglutinin protein) coding sequences were obtained from GeneBank from the National Center for Biotechnology Information online database, and codon optimized for expression in the respective bacterial vectors. For expression in *E. coli*, protein coding sequences were codon-optimized for expression in an *E. coli* system using the Java Codon Adaptation Tool (JCat) codon optimization software (Grote et al., *Nucleic Acids Research*. 33(2): W526-W531, 2005) and synthesized using the incorporated gene synthesis service provided by GenScript with the addition of an N-terminal HIS-tag for downstream protein purification and cloning into the p24a(+) vector. For expression in *B. subtilis*, protein coding sequences were codon optimized for expression in a *B. subtilis* system using JCat codon optimization software and synthesized using the incorporated gene synthesis service provided by GenScript. The resulting synthetic gene construct was cloned into the pTTB2 vector (FIG. 1).

Figure 2:
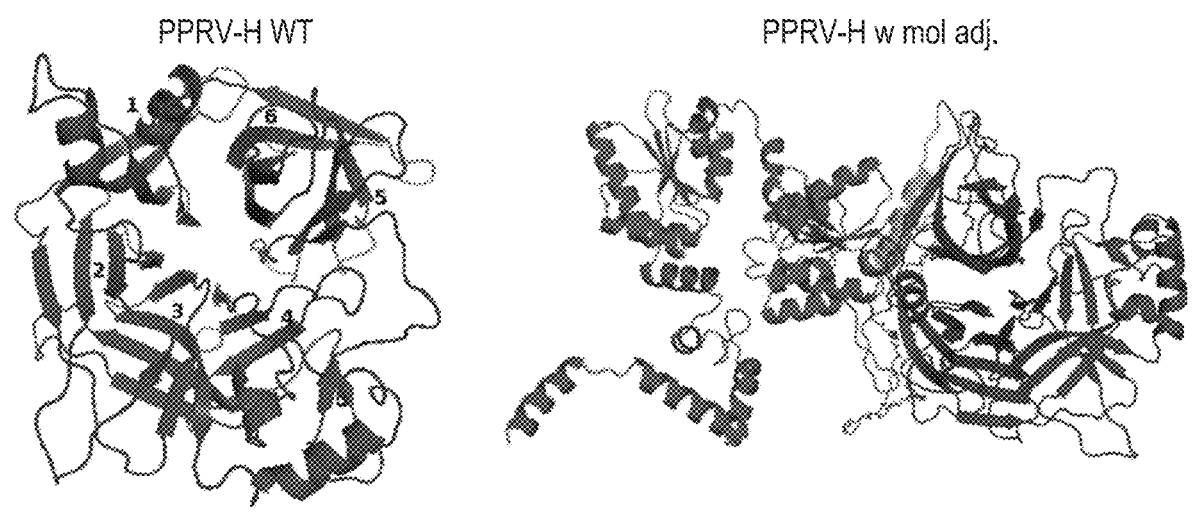

Four different constructs were designed for the testing of an oral PPR vaccine based on the hemagglutinin glycoprotein. Two constructs were expressed in *E. coli* (PPRV-H WT and PPRV-H with molecular adjuvant), and two constructs were expressed in *B. subtilis* (PPRV-H WT and PPRV-H with molecular adjuvant). In silico modeling of the proteins using Pymol, Phyre2, and TMHMM software showed that protein folding was optimal when the molecular adjuvant was cloned at the c-terminal of the PPRV-H protein (FIG. 2).

Example 2 Engineering Vaccine Antigen Expression System

Clonal expansion of PPRV-H inserts in bacterial antigen expression vehicle was confirmed using PCR. PPRV-H sequences were amplified using a forward primer (ATGTCTGCTCAACGTGAACGTA) (SEQ ID: NO 1) and reverse primer (TTAAACAGGGTTGCATGTAACTTC)

Figure 3:
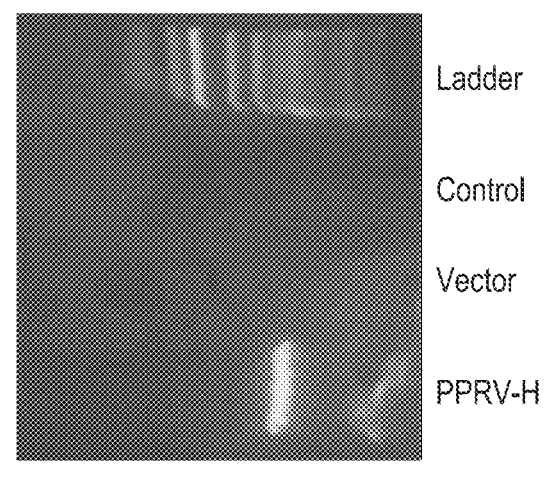

(SEQ ID: NO 2) with CloneAmp HiFi PCR Premix (Takara Bio USA, Inc.), and visualized on an 8% agarose gel (FIG. 3).

Example 3 Composition of Suitable Vaccine Carrier Substrate Material

Vaccine carrier presents as a solid support around which liquid vaccine matrix may be applied. Substrate formulation supporting vaccine administration to monogastric animals is based upon that which is presented and disclosed in the U.S. Pat. No. 10,653,630 "Composition and Method for Reducing Zoonotic Infectious Diseases." The example of the embodiment of vaccine carrier substrate formulation for administration to multi-gastric animals are disclosed below.

In order for a pellet to pass the rumen and proceed to the abomasum, a food pellet must be of no more than 1.5 inches in diameter, and have a low density (Rumen Undegradable Protein (RUP) pellets were used as a substrate base (White Gold Mills, LLC), and were specifically designed to bypass ruminal digestion. RUP pellets were engineered not to exceed a diameter of 0.5 inches.

Example 4 Composition of Vaccine Stabilization and Coating Matrix

Based upon that which is presented and disclosed in the U.S. Pat. No. 10,653,630 "Composition and Method for Reducing Zoonotic Infectious Diseases." Sodium alginate was used at a 2% w/v mix, and calcium lactate was used at a 8% w/v mix.

EXAMPLE 5 Method for Spray Coating Stabilized Vaccine as a Top-dressing onto Substrate Composition Based upon that which is presented and disclosed in the U.S. Pat. No. 10,653,630 "Composition and Method for Reducing Zoonotic Infectious Diseases." Sodium alginate (2%) was applied by spray application onto RUP substrate. Calcium lactate (8%) was subsequently spray applied to yield calcium alginate encapsulation of the composition.

Example 6 Method for Demonstrating Vaccine Stability

Barium sulfate is a radio-opaque salt and will light up on an X-ray, aiding in the visualization of the digestive tract. Administration of barium sulfate either on a pellet or in liquid form. Barium sulfate is highly insoluble and will not be absorbed by the digestive tract. The dosage of solid barium sulfate administration in this study was determined by comparing the liquid dosages used in humans, large dogs, and goats. One study in goats used ~438 g liquid barium sulfate at 70% w/v (Alsafy et al., *J. Med. Sci.* 13(5):316-326, 2013). In comparison, a liquid barium meal in humans used for duodenal imaging is used at a maximum volume at 85% w/v barium sulfate with a maximum dose of approximately 480 g When barium sulfate tablets are used, the quantities are much lower: 700 mg in humans and 1.5 g in large dogs. In contrast to the tablets used in humans, the dog capsules are coated in plastic to protect degradation. The pellets used in this goat study will also be protected with an enteric coating, and the barium sulfate concentrations used in the goat for this study will range from 0.75 g to 20.25 g.

In order to establish the optimal barium sulfate dosage to allow visualization of the pellet location in the goat digestive system, a dosage titration schedule is suggested (Table 1). Pellets will be produced at 125 mg barium sulfate per tablet. Goats are routinely fed dry feed once daily, not to exceed 30% of their daily intake by foraging. At an average of 75 g of dry feed per goat per day, and one pellet weighing a max on 210 mg, a goat would eat ~357 pellets in one sitting. Even at the highest barium sulfate dose, a portion of 162 pellets will be provided to the goat, which is well below the daily dry feed intake.

Four goats were administered barium sulfate incorporated in the enteric coating technology combined with a RUP pellet, and one goat received a liquid dose of barium sulfate using a stomach tube. RUP pellets were coated with a maximum volume of 0.5 inches containing 0.75 g barium sulfate per pellet (Table 1). Goats received a range of 0.75 g to 20.25 g barium sulfate and were compared to a liquid dose of 25 mL/kg at 70% w/v in water (Alsafy et al., *J. Med. Sci.* 13(5):316-326, 2013).

TABLE 1

| Study | Group | # of goats | Treatment | Goat # | Route of Administration | Dose | Dosing schedule | Sampling method | Sampling schedule |
|---|---|---|---|---|---|---|---|---|---|
| X-ray | 1 | 5 | Barium Sulfate | 1 | Liquid | 234.5 g | 1× | X-ray | 2 hrs, 8 hrs, 24 hrs, 32 hrs |
| | | | | 2 | Pellet | 0.75 g | 1× | X-ray | 2 hrs, 8 hrs, 24 hrs, 32 hrs |
| | | | | 3 | Pellet | 1.5 g | 1× | X-ray | 2 hrs, 8 hrs, 24 hrs, 32 hrs |
| | | | | 4 | Pellet | 3.0 g | 1× | X-ray | 2 hrs, 8 hrs, 24 hrs, 32 hrs |
| | | | | 5 | Pellet | 6.0 g | 1× | X-ray | 2 hrs, 8 hrs, 24 hrs, 32 hrs |
| Ivermectin | 2 | 4 | Ivermectin | 1-3 | Pellet | 0.4 mg/kg | 1× | Blood draw | 1 hr, 6 hrs, 24 hrs |
| | | | | 4 | Liquid | 0.4 mg/kg | 1× | Blood draw | 1 hr, 6 hrs, 24 hrs |
| GFP | 3 | 5 | Purified GFP | 2 | S.C. | 10 ug | 1× wk 1, 1× wk 4 | Blood draw | Day 0, 17, 24, 31, 38 |
| | | | *E. coli* GFP | 3 & 6 | Pellet | 1 × 10^11 | 3× wk 1, 3× wk 4 | Blood draw | Day 0, 17, 24, 31, 38 |
| | | | *B. subtilis* GFP | 1 & 4 | Pellet | 1 × 10^11 | 3× wk 1, 3× wk 4 | Blood draw | Day 0, 17, 24, 31, 38 |

TABLE 1-continued

| Study | Group | # of goats | Treatment | Goat # | Route of Administration | Dose | Dosing schedule | Sampling method | Sampling schedule |
|---|---|---|---|---|---|---|---|---|---|
| PPR_1 | 4 | 10 | *B. subtilis* PPRV-H | 1 & 8 | Pellet | 1 × 10^11 | 1× wk 1 | Blood draw | Day 0, 14 |
| | | | *B. subtilis* PPRV-H + adjuvant | 6 & 9 | Pellet | 1 × 10^11 | 1× wk 1 | Blood draw | Day 0, 14 |
| | | | *B. subtilis* PPRV-H | 2 & 11 | Pellet | 1 × 10^11 | 3× wk 1 | Blood draw | Day 0, 14 |
| | | | *B. subtilis* PPRV-H + adjuvant | 3 & 7 | Pellet | 1 × 10^11 | 3× wk 1 | Blood draw | Day 0, 14 |
| | | | *B. subtilis* PPRV-H | 4 | Powder | 1 × 10^11 | 1× wk 1 | Blood draw | Day 0, 14 |
| | | | *B. subtilis* PPRV-H + adjuvant | 10 | Powder | 1 × 10^11 | 1× wk 1 | Blood draw | Day 0, 14 |
| PPR_2 | 5 | 10 | *B. subtilis* PPRV-H | 1-10 | Pellet | 1 × 10^11 | 3× wk 4, 3× wk 12 | Blood draw | Day 28, 35, 42, 80, 88, 92 |

To optimize X-ray visualization of the barium sulfate in the digestive tract, goats were fed dry feed at 8 AM on the day before study start, and allowed forage and water throughout the day and night. Goats were administered Barium Sulfate at 8 AM on study day and X-rays were taken at 2 hrs, 8 hrs, 24 hrs and 32 hrs post administration. After the first imaging session, goats were started back on their regular feeding schedule. X-ray imaging was performed using a miniXray HF8020 High Frequency Ultra Lightmobile X-ray unit. Lateral abdominal X-rays were taken from the right side of the goat, and ventrodorsal X-rays were taken while the goats stood upright on their hind legs. Goats were manually restrained during the X-ray process and no sedatives were required.

All goats ate the barium coated pellets with no reported adverse side effects in response to the Barium Sulfate, restraint or X-ray imaging. Goat #1, which received liquid formulation, showed a clear outline of the intestinal tract with staining of the abomasum at two hours and manure staining in the small intestine starting at eight hours that intensified until 32 hours post administration (FIG. 4A-H images are lined up to show head (left) to tail (right) orientation with stars illustrating barium accumulation at the gastrointestinal lining). The four remaining goats, which received pellets coated with barium sulfate, all showed barium sulfate passage past the Rumen at two hours (FIG. 4 I-J with stars showing barium localization in both the Omasum and Rumen). At eight hours, Omasal and Abomasal localization could be observed (FIG. 4 K-L) and at 24- and 32-hour time points most barium was dissolved with manure staining in the colon and small intestine (FIG. 4 M-P).

In addition to gastro-intestinal imaging, manure was imaged to determine barium intermixing. At 8 hours, manure in all goats was radio opaque indicating that the barium was fully mixed with the excrement. Goats receiving coated pellets (FIG. 5 intra image labels A-B) were administered only a fraction (0.3-8.6%) of the total barium dose administered using liquid (FIG. 5 intra image label C) resulting in the manure of goats that received pellets showing a reduced intensity. Presence of barium at 8 hours in the manure of goats receiving solid barium supports solids bypassing the rumen, mimicking the path through the gastrointestinal tract of a liquid.

To determine whether the oral administration in the pellet form allows for uptake of a substrate in the blood (i.e. the pellet is retained in the small intestines sufficiently long), pellets were treated with 1-methylimidazole (Ivermectin, M0508, Fisher), a routinely used anthelmintic in live-stock typically administered orally in liquid form, and combined it with the proprietary enteric coating. As Ivermectin is metabolized by the liver and can be detected in the blood stream, HPLC analysis was performed to detect the plasma concentrations in the goats.

In goats, Ivermectin is used orally at a dose of 0.3 mg/kg (per the protocols as defined in the Georgia Dairy Goat Breeders Association), averaging to a dose of 7.5 mg for a 25 kg goat. For this study, pellets will be coated using a dose of 3.75 mg/pellet, and goats will be weighed before administration to ensure proper dosing.

Four goats were administered a 0.4 mg/kg Ivermectin dose with 3 goats dosed using pellets and 1 goat was dosed using the traditional liquid formulation (Table 1). Liquid was administered using a 5 mL syringe and squirting into the back of the goat's mouth. Goats were randomly assigned to treatment groups, and weighed before administration to ensure proper dosing. Goats were not fasted, and Ivermectin was administered at 8 AM after which normal dry feed was provided. All goats were allowed free access to forage and water throughout. Blood samples (15 mL) were collected into heparinized tubes from the jugular vein at 1, 6, and 24 hrs post dosing. Baseline blood was collected one day prior to study start. Detection of plasma Ivermectin concentration was performed according to the protocol described by Morbidelli et al. (Morbidelli et al., *MethodsX.* 5:1503-1507, 2018). In short, four parts of acetonitrile and one-part $ddH_2O$ were added to four parts serum and mixed for 30 minutes. After five minutes of centrifugation at 2000 g, supernatant was transferred into clean tube and solid phase was derived by drying using nitrogen flow. For derivatization, residue was dissolved in N-methylimidazole/acetonitrile (1:2 v/v). Samples were incubated with triflouroacetic acid/acetonitrile (1:2 v/v) and incubated for 30 minutes before injection into the chromatograph.

Goats were dosed with Ivermectin according to weight (Table 1). RUP pellets were impregnated with Ivermectin and coated using ruminal protective coating. Goat samples showed negative sera prior to Ivermectin administration as well as 1 hr post administration (FIG. 6).

The solid administration of Ivermectin (pellet) is at least as good as the liquid administration. Animals receiving higher dosages also showed higher blood plasma levels, indicating a dose-response relationship. The results indicate that administration of a compound using the enteric coating successfully releases the Ivermectin post-rumen, allowing for uptake in the blood.

As a proof of concept to study the feasibility of using an orally delivered antigen for vaccination strategies in ruminants, two bacterial vectors (*E. coli* and *B. subtilis*) were engineered to express the GFP protein. Four goats each received a prime and a boost sequence of bacterial vehicle with GFP, and one goat received a prime and a boost of subcutaneous injected purified GFP protein (Table 1).

The pellets will be used to present an antigen to the goat, and serum antibodies (IgG) will be measured. This shows that seroconversion can be achieved in a goat using oral presentation of an antigen. Goats are widely used to create antibodies for laboratory practice, and are being used because a goat will on average produce 20 mg IgG per mL blood. Since GFP is a foreign substance to a goat and has been successfully used in goats by multiple companies to raise anti-GFP antibodies, a bacterial antigen expression vehicle presenting GFP will be used on the pellet.

For the purpose of this study, we will create pellets with increasing GFP dosages. Each pellet will be coated based on CFU (Table 1). As a control, two goats will be injected subcutaneously with purified protein at the highest dose. Goats will be given GFP pellets for three days during the first week (M-T-W), and third week. Blood (15 mL) will be drawn from the jugular vein by a skilled veterinarian at day 0 (pre-bleed), 14, 34, and 42. Blood will immediately be centrifuged and separated into three fractions (RBC, QBC, Plasma), and stored at −20° C. until analysis.

Figure 7:
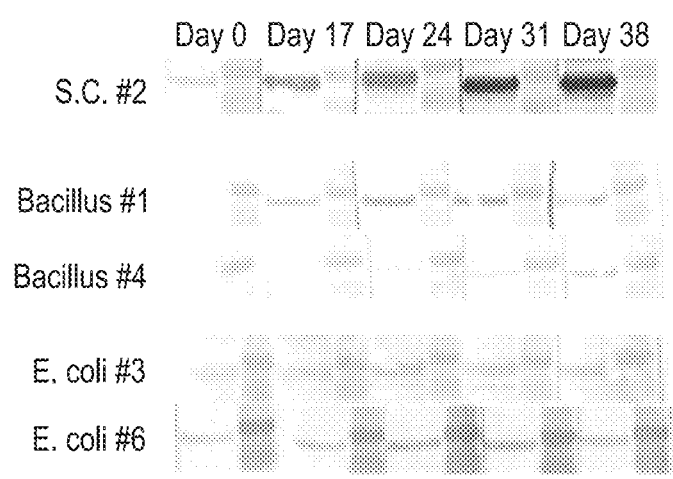
FIG. 7 shows goats that were orally vaccinated all showed a serum anti-GFP IgG antibody response.

To test for antibody presence in the goats, purified GFP protein was loaded onto SDS-PAGE gels and transferred onto PVDF membranes. Membranes were incubated with goat serum from respective days and an anti-Goat IgG antibody was used to detect antibody presence. GFP protein size is 27 kDa and a band was observed in all samples at this size (FIG. 7, blue=30, pink=25 kDa). Some background was observed at day 0 in goats receiving GFP purified from or expressed by *E. coli*, which is due to the fact that the GFP protein used for the western blot was purified out of *E. coli*, and the use of unpurified goat serum. Upon vaccination using GFP vaccine, all goats showed an increase in the band appearing at 27 kDa, indicating generation of serum antibodies. Goat #2, which received subcutaneous injection, showed the strongest reaction as indicated by darker bands. Goats that were orally vaccinated all showed a serum anti-GFP IgG antibody response (FIG. 7).

Example 7—Methods for Demonstrating Vaccine Efficacy

For the development of an oral PPR vaccine, we used a recombinant vaccine employing a bacterial antigen expression vehicle, presented as an encapsulated bacterin (inactive) harboring the PPRV-H glycoprotein. Four different constructs were designed for the testing of an oral PPR vaccine based on the hemagglutinin glycoprotein. Two constructs were expressed in *E. coli* (PPRV-H WT and PPRV-H with molecular adjuvant), and two constructs were expressed in *B. subtilis* (PPRV-H WT and PPRV-H with molecular adjuvant). In silico modeling of the proteins using Pymol, Phyre2, and TMHMM software showed that protein folding was optimal when the molecular adjuvant was cloned at the c-terminal of the PPRV-H protein (FIG. 2).

Figure 8:
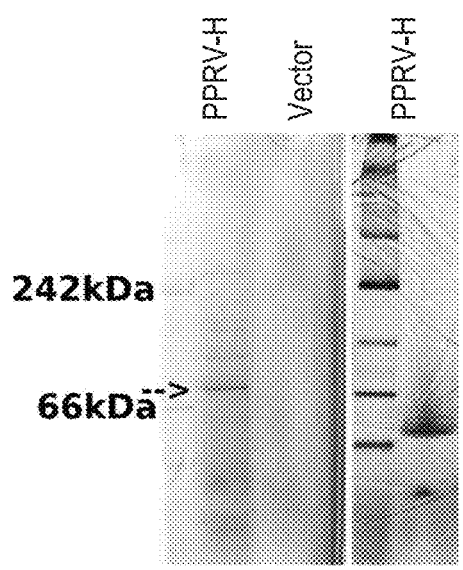
FIG. 8 is a gel showing B. subtilis cells, showed protein expression as well as post-translational glycosylation, which could be removed by Endo-H treatment.

To confirm construct integration in the bacterial antigen expression vehicle, DNA was isolated from transformed *E. coli* and *B. subtilis* cells and subjected to restriction enzyme digestion and PCR amplification (FIG. 3). To confirm protein expression and post-translational modification in the bacterial antigen expression vehicle, whole protein lysates were run on SDS-PAGE and Native Page gels, stained with Coomassie Blue or Silver staining. Though *E. coli* cells integrated the PPRV-H constructs, they failed to express the PPRV-H protein. *B. subtilis* cells, however, showed protein expression as well as post-translational glycosylation, which could be removed by Endo-H treatment (FIG. 8). Goats were given either PPRV-H alone or in combination with a biosynthetically engineered molecular adjuvant (Table 1), lipopolysaccharide (LPS) from *E. coli*.

Vaccine was presented either in combination with a RUP Pellet or as a powder. Due to palatability issues, the powder formulation was discontinued after the first round. Two groups also got RUP pellets only one day of the week, but consumption was found to be increased on the third day of the week, and therefore all goats were placed on three times a week schedule going forward. Goat serum was checked against the vaccine after the first round, and serum antibodies were found only in the non-adjuvanted formulation administered three times a week. Therefore, during rounds two and three, all goats received the same vaccine, namely PPRV-H on the RUP pellets, 3× a week.

Figure 9:
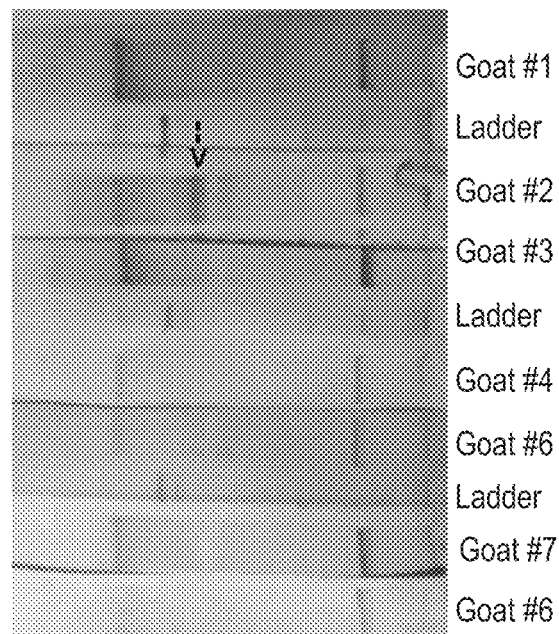
FIG. 9 is a gel showing goat serum was tested on western blot for binding against the vaccine, and Goat #2, who had received two doses of the PPRV vaccine (compared to other goats receiving only one dose) showed an antibody response.
Figure 10:
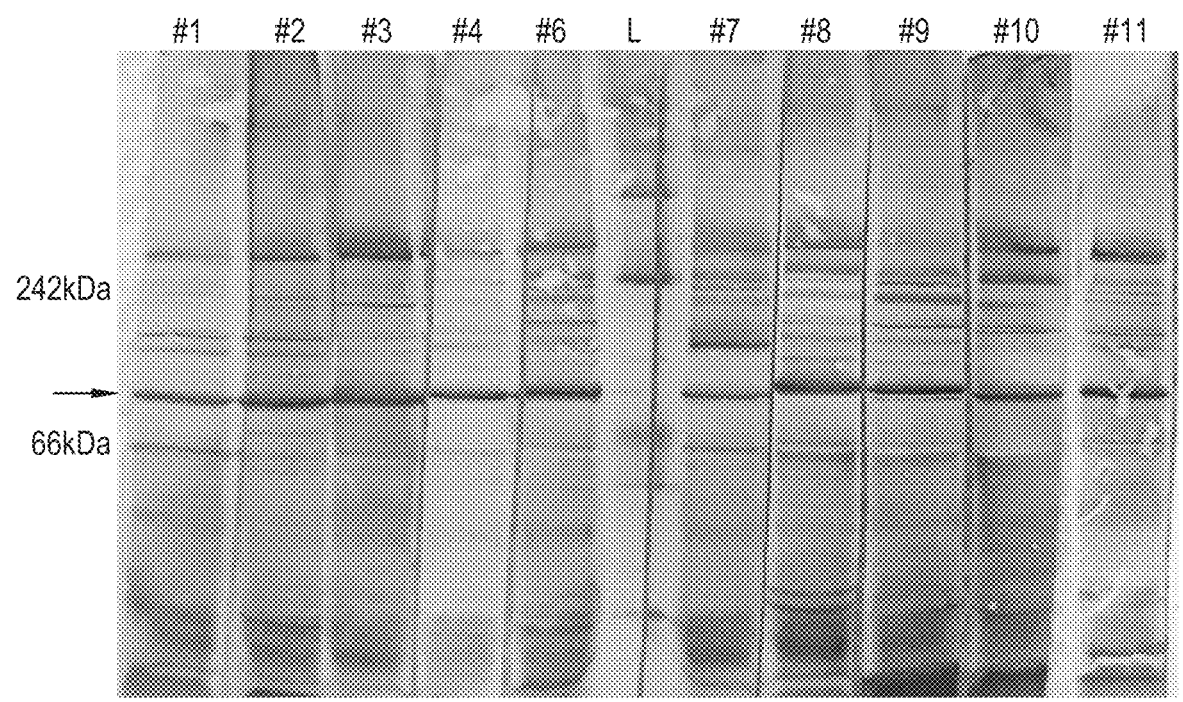
FIG. 10 is a gel showing all goats showed a strong antibody response (selective binding at −70 kDa).

After the second round, goat serum was tested on western blot for binding against the vaccine, and Goat #2, who had received two doses of the PPRV vaccine (compared to other goats receiving only one dose) showed an antibody response (FIG. 9). Therefore, after an eight-week interval, all goats received a second boost with the PPRV-H vaccine, and serum was checked one-week post dosing. At this time, all goats showed a strong antibody response (selective binding at ~70 kDa, FIG. 10).

REFERENCES

Alsafy et al., "Contrast Radiographic, Ultrasonographic and Computed Tomographic Imaging Studies on the Abdominal Organs and Fatty Liver Infiltration of Zaraibi Goat", *J. Med. Sci.* 13(5):316-326, 2013.

Grote et al., "JCat: a Novel Tool to Adapt Codon Usage of a Target Gene to its Potential Expression Host", *Nucleic Acids Research.* 33(2):W526-W531, 2005.

Baron et al., "Peste des Petits Ruminants virus", *Adv Virus Res.* 95:1-42, 2016.

Chen and Cerutti, "Vaccination Strategies to Promote Mucosal Antibody Responses", *Immunity.* 33:479-491, 2010.

Choppin and Scheid, "The role of viral glycoproteins in adsorption, penetration, and pathogenicity of viruses", *Rev Infect Dis.* 2:40-61, 1980.

Herbert and Baron, "Recombinant adenovirus expressing the haemagglutinin of peste des petits ruminants virus (PPRV) protects goats against challenge with pathogenic virus; a DIVA vaccine for PPR", *Vet Res.* 45:24, 2014.

Herrero et al, "The roles of livestock in developing countries", *Animal.* 7 Suppl 1:3-18, 2013.

Fujkuyama et al., "Novel Vaccine Development Strategies for Inducing Mucosal Immunity", *Expert Rev Vaccines.* 11(3): 367-379, 2012.

Mariner et al., "The opportunity to eradicate Peste des Petits Ruminants", *J Immunol.* 196:3499-3506, 2016.

Mazzitelli et al., "Production and Characterization of Alginate Microcapsules Produced by a Vibrational Encapsulation Device", *J. Biomat. Appl.* 23:123-145, 2008.

Morbidelli et al., "A quick and simple method for the determination of Ivermectin in dog plasma by LC/MS", *MethodsX.* 5:1503-1507, 2018.

Neutra and Kozlowski, "Mucosal Vaccines: the Promise and the Challenge", Nature *Rev. Immunol.* 6: 148-158, 2006.

Ogra et al., "Vaccination Strategies for Mucosal Immune Responses", *Clin. Microbiol. Rev.* 14(2): 430-445, 2001.

Rojas et al., "Vaccination with recombinant Adenoviruses Expressing the Peste des Petits Ruminants Virus F or H Proteins Overcomes Viral Immunosuppression and Induces Protective Immunity against PPRV Challenge in Sheep", *PLoS One.* 9(7): e101226, 2014.

Schulte-Herbruggen et al., "Rural protein insufficiency in a wildlife-depleted West African farm-forest landscape", *PLoS One.* 13; 12(12):e0188109, 2017.

Woodrow et al., "Mucosal Vaccine Design and Delivery", *Annu. Rev. Biomed. Eng.* 14: 17-46, 2012.

We claim:

1. A vaccine for oral administration comprising: an expression vehicle comprising *Bacillus subtilis* expressing a hemagglutinin protein from Peste-des-Petits-Ruminants virus (PPRV).

2. A vaccine coated solid support made by a process comprising:
   stabilizing said hemagglutinin protein from Peste-des-Petits-Ruminants virus (PPRV) within a liquid carrier matrix;
   coating the stabilized hemagglutinin protein from Peste-des-Petits-Ruminants virus (PPRV) on to a solid support; and
   encapsulating said hemagglutinin protein from Peste-des-Petits-Ruminants virus (PPRV) on the surface of said solid support by adding a cross-linking agent.

3. The vaccine of claim 2, wherein the solid support is comprised of a ruminant undegradable protein (RUP).

4. The vaccine of claim 2, wherein the crosslinking agent is a divalent cation salt of calcium.

5. A vaccine antigen expression system comprising:
   a bacterial antigen expression vehicle comprising *Bacillus subtilis*, said bacterial antigen expression vehicle configured to express one or more recombinant viral protein antigens, wherein the one or more recombinant viral protein antigens are engineered from a hemagglutinin protein from Peste-des-Petits-Ruminants virus (PPRV) and a vaccine carrier substrate.

* * * * *